United States Patent [19]
Jacobson et al.

[11] Patent Number: 5,626,619
[45] Date of Patent: May 6, 1997

[54] OPTICALLY ISOLATED SHOCK CIRCUIT FOR IMPLANTABLE DEFIBRILLATOR

[76] Inventors: Peter Jacobson, 4, Route de Marienthal, 67500 Haguenau; Daniel Kroiss, 22, Rue Georges Clemenceau, 67590 Schweighouse-Moder; Alan Ostroff, 21, Rue de l'Eglise, 67250 Preuschdorf, all of France

[21] Appl. No.: 320,874

[22] Filed: Oct. 11, 1994

[30] Foreign Application Priority Data

Oct. 8, 1993 [FR] France ................... 93 11993

[51] Int. Cl.$^6$ ........................... A61N 1/39
[52] U.S. Cl. ........................... 607/5; 607/7
[58] Field of Search ............. 607/4, 5, 6, 15, 607/16, 37

[56] References Cited

U.S. PATENT DOCUMENTS

| | | | |
|---|---|---|---|
| Re. 27,652 | 5/1973 | Mirowski et al. | 128/419 D |
| 3,742,947 | 7/1973 | Hashem | 128/696 |
| 3,945,387 | 3/1976 | Adams | 128/419 PG |
| 4,384,585 | 5/1983 | Zipes | 607/5 |
| 4,403,612 | 9/1983 | Fogarty | 606/194 |
| 4,504,773 | 3/1985 | Suzuki et al. | 607/5 |
| 4,614,192 | 9/1986 | Imran et al. | 607/5 |
| 4,800,883 | 1/1989 | Winstrom | 607/7 |
| 4,823,796 | 4/1989 | Benson | 607/7 |
| 4,998,531 | 3/1991 | Bocchi et al. | 607/5 |
| 5,111,816 | 5/1992 | Pless et al. | 107/4 |
| 5,163,427 | 11/1992 | Keimel | 607/5 |
| 5,265,588 | 11/1993 | Nelson et al. | 607/5 |
| 5,285,779 | 2/1994 | Cameron et al. | 607/5 |
| 5,366,485 | 11/1994 | Kroll et al. | 607/5 |
| 5,405,361 | 4/1995 | Persson | 607/5 |
| 5,488,553 | 1/1996 | Renger | 607/5 |

FOREIGN PATENT DOCUMENTS

| | | | |
|---|---|---|---|
| 0281219 | 1/1988 | European Pat. Off. | A61N 1/39 |
| 0280526 | 2/1988 | European Pat. Off. | A61N 1/39 |
| 0324380 | 1/1989 | European Pat. Off. | A61N 1/39 |
| 0326290 | 1/1989 | European Pat. Off. | A61N 1/38 |
| 0362093 | 7/1989 | European Pat. Off. | A61N 1/39 |
| 0473002 | 8/1991 | European Pat. Off. | A61N 1/08 |
| 0536873 | 7/1992 | European Pat. Off. | A61N 1/39 |
| 0553864 | 1/1993 | European Pat. Off. | A61N 1/39 |
| 2257312 | 1/1997 | France | A61N 1/36 |
| 1149979 | 8/1983 | U.S.S.R. | A61N 1/36 |

OTHER PUBLICATIONS

Schuder J.C. et al., "Ultrahigh–energy hydrogen thyratron/SCR bidirectinal waveform defibrillator", Medical & Biological Engineering & C, vol. 20, No. 4, Jul. 1982, pp. 419–424.

Schuder J.C. et al., "Transthoracic Defibrillation of 100 KG Calves With Biodirectional Truncated Exponential Shocks", Vol. XXX, May 2–4, 1982, pp. 520–525.

Jones J.L. et al., "Decreased defibrillator–induced dysfunction with biphasic rectangular waveforms", American Journal of Physiology, vol. 247, Nov. 1984, pp. H793–H796.

*Primary Examiner*—William E. Kamm
*Assistant Examiner*—Carl H. Layno
*Attorney, Agent, or Firm*—Orrick, Herrington & Sutcliffe

[57] ABSTRACT

A defibrillator output circuit utilizes an optically coupled signal for controlling an isolated electronic switch. Variants of the output circuit include coupling via phototransistors or photodiodes for the control of at least one electronic switch. An H-bridge circuit configuration with four switches is connected to a single energy storage capacitor for generating multiphasic shocks across a load. The polarity of the shocks is selectable. Optical coupling methods are employed for driving the high side switches in the H-bridge.

58 Claims, 5 Drawing Sheets

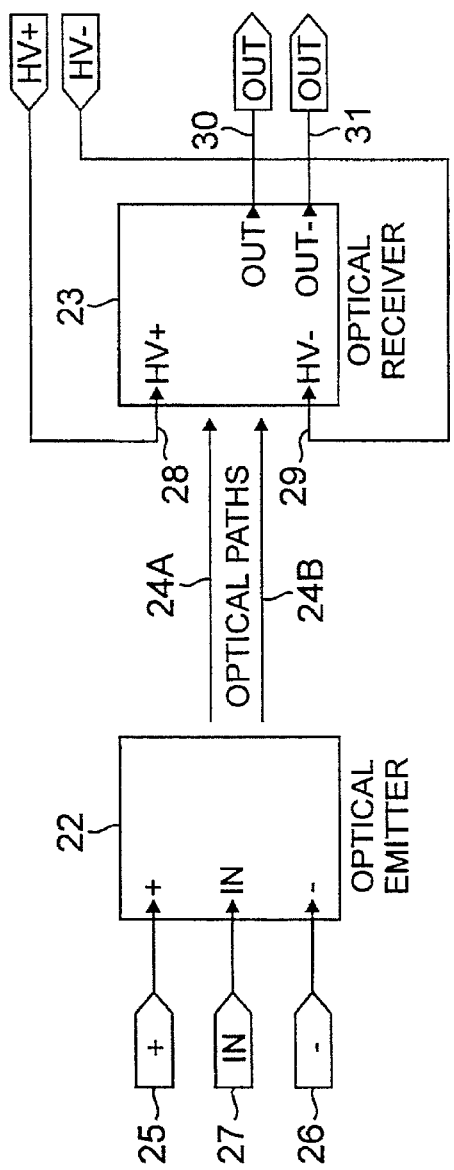
FIG. 2
FIG. 3
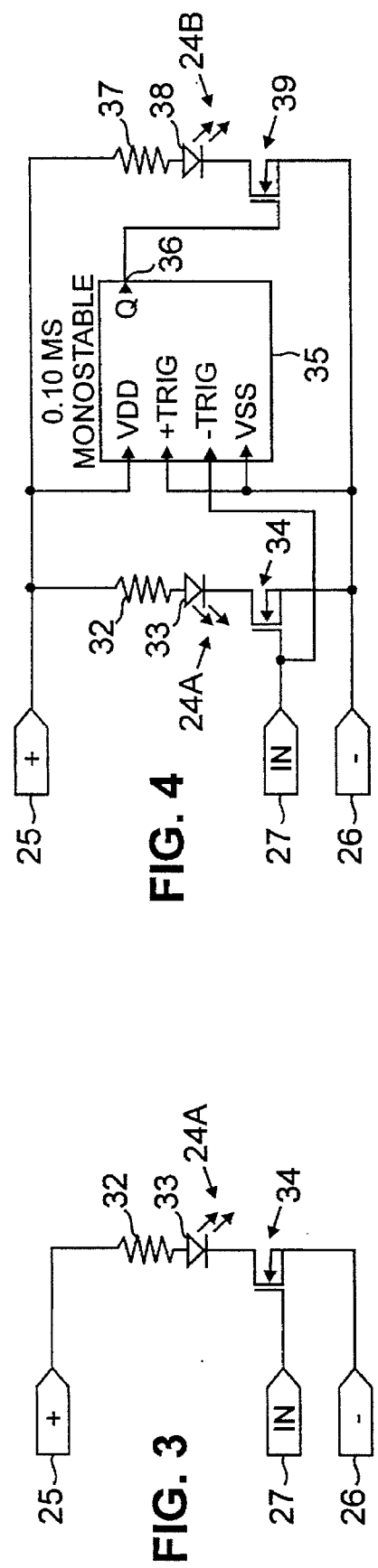
FIG. 4

OPTICALLY ISOLATED SHOCK CIRCUIT FOR IMPLANTABLE DEFIBRILLATOR

FIELD OF THE INVENTION AND DEFINITIONS

The present invention relates to delivering high energy shocks in an implantable defibrillator, and more particularly to driving electrically isolated electronic switches in an implantable defibrillator. The invention can be advantageously applied to delivering monophasic or multiphasic truncated shocks to a load from a single capacitor.

In the specification and claims, the following terms are used. A "defibrillator" refers to any device intended to revert a tachyarrhythmia with electrical energy substantially exceeding the energy provided by implantable cardiac pacemakers, including any combination or subset of implantable defibrillators, cardioverters, and pacemakers. A "monophasic" shock delivers current in one direction. A "multiphasic" shock delivers current first in one direction or polarity (called the first phase of the shock) and then in the opposite direction or polarity (called the second phase), and may provide additional phases which typically alternate polarity. A "biphasic" shock provides two phases. A "truncated" shock abruptly stops delivering current to the load, either by interrupting the current in the load or by rapidly discharging the storage capacitor. The "load" represents the impedance of lead wires, defibrillation or shock electrodes, the shock electrode-tissue interface, and tissue bulk between the shock electrodes. A "single capacitor" and a "capacitor" represent any one capacitor or more than one capacitor in a series and/or parallel combination of capacitor packages, which results in a single equivalent capacitor with two terminals connected to the shock circuit.

The invention pertains to shock generators for monophasic and multiphasic waveforms, including biphasic waveforms. It applies to generators of single-capacitor multiphasic waveforms and to generators of multiple-capacitor multiphasic waveforms. The single-capacitor waveform discharges a single capacitor through the load in a first direction in the first phase, interrupts the current, discharges the single capacitor still further through the load in the opposite direction in the second phase, and then truncates. In consequence, second phase leading edge amplitude typically equals first phase trailing edge amplitude. The multiple-capacitor waveform discharges a different single capacitor for each direction, or even for each phase, so that the leading edge amplitude does not necessarily depend on the trailing edge amplitude of the preceding phase.

BACKGROUND OF THE INVENTION

Early defibrillators provided only monophasic waveforms. USRE27652 to Mirowski (priority 09 Feb 70) refers to an automatic defibrillator with a monophasic shock circuit which delivered an untruncated shock as soon as the storage capacitor charged to a fixed voltage (no isolated control signal was needed). FR2257312 to Zacouto (priority 16 Jan 74) refers to providing sequential monophasic shocks over multiple electrode pairs, also not isolating control. U.S. Pat. No. 4,403,614 to Engle (priority 19 Jul. 79) and U.S. Pat. No. 4,384,585 to Zipes (priority 06 Mar 81) referred to synchronizing shock with detected events, but did not show any details of the discharge circuit. U.S. Pat. No. 4,614,192 to Imran (priority 21 Apr. 82) refers to truncating monophasic shocks by rapidly discharging the storage capacitor. The shock switch and driver consisted of a pulse transformer driving a silicon controlled rectifier (SCR), a pulse transformer controlling a thyristor.

Following experiments with bidirectional shocks in 1964 and 1980, J. C. Schuder et al. described an "Ultrahigh-energy thyratron/SCR bidirectional waveform defibrillator", in Med Biol Eng Comput 20:419, 1982, having a biphasic generator with one capacitor per phase. SU1149979 to Pekarski (priority 08 October 83) also refers to a biphasic truncated shock circuit with one capacitor for each phase.

In 1984, Schuder et al. presented results of a simulated single-capacitor truncated biphasic waveform. In their paper entitled "Transthoracic Defibrillation of 100 Kg Calves with Bidirectional Truncated Exponential Shocks", Vol XXX Trans Am Soc Artif Intern Organs, 1984, the authors referred to experiments made with an "asymmetrical truncated exponential biphasic waveform . . . which can be implemented in a clinical sized apparatus." They showed a waveform where the trailing edge of the first phase was equal to the leading edge of the second phase.

The single capacitor approach simplifies both charging and discharging circuits, reducing size, weight, and unreliability in implantable devices. As data accumulated showing improved animal and clinical results with biphasic truncated shocks, compared to monophasic truncated shocks, there have been proposed a variety of single-capacitor multiphasic truncated waveform generators. All such circuits include at least four switches in an H-bridge configuration (also referred to herein as an "H-bridge switch").

Designers frequently employ the H-bridge configuration for driving a load in two directions from a DC source, for example, driving a stepper or servo motor from a battery. In the first phase a first switch connects the positive source pole to a first side of the load and a second switch connects the negative source pole to the second side of the load. In the second phase a third switch connects the positive source pole to the second side of the load, and a fourth switch connects the negative source pole to the first side of the load. The first and third switches, connected to the positive source pole, are called high side switches. The second and fourth switches, connected to the negative source pole, are called low side switches.

Prior art implantable discharge circuits employ one or more of three types of switches in the H-bridge. Each type of switch has an input, output, and control terminal, and responds to a control signal between the control and output terminals. Silicon controlled rectifiers (SCRs) turn on in response to a pulse on the control terminal, but only turn off when current through them falls essentially to zero. Metal-oxide-semiconductor field effect transistors (MOSFETs) and insulated-gate bipolar transistors (IGBTs) remain on while a control voltage appears at the control terminal.

Depending on how they protect pacing and sensing circuits from defibrillation pulses, prior art circuits either isolate the capacitor and discharge circuit from pacing and sensing ground, or they connect the negative side of the capacitor to ground. In the isolated version they must provide isolated switch control signals. In the negative-ground version, they must still provide isolated control signals to the high side switches.

Thus, any single capacitor biphasic shock delivery circuit needs: two high side switches and two low side switches connected in an H-bridge, and at least two isolated switch drivers. The following prior art patents all disclosed an H-bridge for generating a single-capacitor multiphasic waveform, where the structure for the H-bridge switches and the switch control drivers differ in each design.

U.S. Pat. No. 4,800,883 to Winstrom (priority 02 April 86) refers to an isolated discharge circuit with four MOSFET switches, and a transformer with an RF carrier, rectification, and rapid shutoff circuits for high and low side drivers. A single transformer with two secondaries drives both high and low side switches in the same phase. A multilevel capacitor with voltage taps is described.

EP0281219 to Mehra (priority 14 Jan 87) refers to a negative-ground discharge circuit with an SCR in series with a MOSFET for each high side switch and an SCR for each low side switch. Mehra did not give details of the switch drivers.

EP0280526 to Baker (priority 27 Feb 87) refers to using the Winstrom circuit above, with the additional requirement of a first phase duration that is longer than the second phase duration (note that in 1984 Jones et al. published results for defibrillation pulses with a 5 ms first phase and a 1 ms second phase, see Am. J. Physiol. 247 (Heart Circ. Physiol. 16)). Baker also refers to providing protection against a short-circuited load, by opening the H-bridge switches when the load current exceeds a preset value.

EP0324380 to Bach (priority 12 Jan 88) provided another negative-ground discharge circuit, with SCRs for high side switches and MOSFETs for low side switches. Bach used pulse transformers for high side drivers and drove the low side directly. Bach included diodes in series with low side switches to protect against external defibrillators.

EP0326290 to de Coriolis (priority 19 Jan 88) provided yet another negative-ground discharge circuit, with two SCRs in series for the first phase high side switch, a MOSFET for the first phase low side switch, and SCRs for the second phase high and low side switches. de Coriolis truncated the second phase by rapidly discharging the storage capacitor through the first phase high side switch and the second phase low side switch. de Coriolis drove the high side switches with pulse transformers and the low side switches with level shifters referred to a positive supply.

U.S. Pat. No. 4,998,531 to Bocchi (priority 28 Mar 90) provided still another negative-ground discharge circuit, with four MOSFET switches. Each MOSFET switch had a series diode to prevent reverse current during external defibrillation. Bocchi used level shifters for low side drivers and used a transformer for the high side driver, where a pulse in one direction turned the MOSFET on, and a pulse in the other direction turned the MOSFET off.

U.S. Pat. No. 5,111,816 to Pless (priority 22 October 90) provided yet another negative-ground discharge circuit, with IGBT or MOSFET switches. All Pless variants drive both high and low side switches in the same phase from a common transformer with an RF carrier and rectification, and a rapid shutoff circuit for at least one switch in each phase. Pless also referred the negative battery terminal to ground and inverted this to make the pacing voltage.

All prior art designs either isolate the discharge circuit from pacing and sensing ground, or refer the negative pole of the storage capacitor to pacing and sensing ground. This requires electrically isolating control signals for high side switches. A problem with the prior art designs is that they use transformer coupling for isolation. They use pulse transformers to drive SCRs, and either pulse transformers or RF transformers with rectification and a rapid shutoff circuit to drive MOSFETs or IGBTs.

The disadvantages of such transformer coupling include magnetic coupling from other inductors or transformers in the implant, such as the transformer which charges the energy storage capacitors; magnetic coupling to sensitive circuits elsewhere in the implant, such as current loops in the high-gain R-wave sensing circuits; relatively bulky and expensive magnetic components which cannot be implemented using integrated circuit technology; the possibility of transformer core saturation in a strong external DC magnetic field, including fields produced by permanent magnets commonly used to test pacemakers and defibrillators; and magnetic coupling from strong external AC magnetic fields, such as fields produced by industrial heating or welding apparatus.

In prior art designs the transformer also required complex and power-hungry additional radio frequency oscillator or pulse driver circuits.

There is thus a continuing need for improvement of high-voltage shock circuits for use in implantable defibrillators.

SUMMARY OF THE INVENTION

It is, therefore, an object of this invention to overcome the aforementioned disadvantages in control circuitry for high voltage shock switches by providing optically isolated control for the electrically isolated electronic switches.

Optical control in accordance with the present invention is achieved by providing a transmitter for converting an electrical signal to an optical signal, an electrically isolated optical path, and a receiver for converting the optical signal to an electrical signal.

One variant of the invention provides an optical communication path for the control signal for each switch, where the presence of the optical signal instructs the receiver to turn on the controlled switch, and its absence instructs the receiver to turn it off. Stated otherwise, the optical signal may have a first intensity magnitude for a time, relative to a selected threshold, that corresponds to the duration the electronic switch is to be closed to deliver a shock (the "presence") and otherwise has an intensity magnitude that is below the threshold so that the switch is open and no shock energy is delivered to the load (the "absence"). Typically, in the "present" state, the optical signal is on at some value corresponding to a selected logic high level, and in the absent state, the optical signal at a logic low level corresponding to an off state where there is no optical signal.

A second variant of the invention provides two optical communication paths for controlling each isolated switch, where the presence of a signal on the first path instructs the receiver to turn on the controlled switch, and the presence of a second optical signal on the second path instructs the receiver to turn off the controlled switch. In this variant the "presence" of an optical signal may be a pulse of light, or it may be a relative change of intensity, i.e., an optical signal present for the appropriate "switch on" duration. It is preferred to use short pulses at least to open the switch to minimize power consumption.

It is a further object of this invention to provide photo-responsive optical receiver circuits for an isolated switch control. One variant of the receiver circuit provides a floating power supply and a photodetector that is a phototransistor for applying charging current to the control terminals of the controlled isolated switch in response to an optical control signal. Another variant provides one or more photodetectors that are photodiodes for performing the same function.

It is yet another object of this invention to provide shutoff circuits to turn off the controlled switch rapidly in response to a particular state of the optical control signal or signals.

In one embodiment, the invention is directed to a shock delivery circuit for use in an implantable defibrillator, which includes a battery for supplying energy, control circuits having electrical signal outputs for timing shocks, a shock charging circuit for converting battery energy to shock energy, a high voltage capacitor for storing shock energy, an electronic switch for connecting the capacitor to a load, and means for actuating said electronic switch such that switch control is obtained using optical isolation. Preferably, the actuating means is an optical isolation circuit that operates the electric switch without direct electrical control. One such isolation circuit includes an optical transmitter, such as a photoemitter, to convert at least one electrical signal from said control circuits to at least one optical signal, an optical receiver, such as a photodetector, to convert the at least one optical signal to at least one electrical signal for selectively turning on and turning off (i.e., closing and opening) the electronic switch, and an electrically isolated optical path conveying each optical signal from the optical transmitter to the optical receiver.

According to one embodiment of the present invention, the optical transmitter (photoemitter) emits an optical signal whose presence signals the optical receiver to turn on the electronic switch, and whose absence signals the optical receiver to turn off the electronic switch. More preferably, the optical receiver includes a power supply, for providing power for charging the control terminals of the electronic switch, a first phototransistor switch for selectively conducting a charging current from the power supply to the control terminals of the electronic switch, in response to the presence of an optical signal, to turn on said electronic switch, and a shutoff circuit for selectively discharging the control terminals of the electronic switch, in response to the absence of said current for charging, to turn off the electronic switches.

The power supply preferably includes a capacitor for storing energy at low voltage, a current-limited path, having at least one high-value resistor, for charging the capacitor for storing energy at low voltage from the capacitor for storing shock energy, and a voltage limiter to prevent the capacitor for storing energy at low voltage from charging to a voltage level beyond a preset voltage limit. The voltage limiter is preferably a zener diode with a zener voltage of, e.g., approximately 15 V. In this embodiment, the shutoff circuit includes a circuit means, such as a transistor for discharging the control terminals of the electronic switch, when the power supply and phototransistor no longer produce the charging current.

In an alternate embodiment of the optical isolation circuit using a single optical signal to control the switch, the optical receiver includes at least one photodiode, for selectively providing a charging current to the control terminals of the electronic switch in response to the presence of the optical signal, to turn on the electronic switch, and a shutoff circuit for selectively discharging the control terminals of the electronic switch, in response to the absence of said current for charging from the one or more photodiodes and turn off said electronic switch. In this embodiment, the shutoff circuit preferably includes a transistor for discharging the control terminals of said electronic switch when the photodiode (or photodiodes) no longer produce the charging current to the control terminals of the electronic switch.

In the alternate embodiment of the optical isolation circuit which uses more than one optical signal to control the switch, the optical transmitter emits a first optical signal whose presence signals to the optical receiver to turn on the electronic switch, and emits a second optical signal whose presence signals the optical receiver to turn off the electronic switch. In this embodiment of the optical isolation circuit, one embodiment of the optical receiver includes a power supply, for providing power for charging the control terminals of the electronic switch, a first phototransistor switch for selectively conducting power from the power supply to the control terminals of the electronic switch, in response to the presence of the first optical signal, to turn on the electronic switch, and a shutoff circuit for selectively discharging the control terminals of the electronic switch, in response to the presence of the second optical signal and turn off said electronic switch.

One such shutoff circuit includes a first phototransistor activated by the first optical signal to turn on the electronic switch, as already described, and a second phototransistor, actuated by the second optical signal, connected to discharge the control terminals of the electronic switch when activated. The shutoff circuit also preferably includes a resistor across the control terminals of the electronic switch to prevent charge buildup on said control terminals when neither optical signal is present.

In a second version of this alternate embodiment, the optical receiver includes at least one photodiode, for selectively providing a charging current to the control terminals of the electronic switch, in response to the presence of the first optical signal, to turn on the electronic switch and a shutoff circuit for selectively discharging the control terminals of electronic switch, in response to the presence of the second optical signal, and turn off said electronic switch. One such shutoff circuit includes a phototransistor, actuated by the second optical signal, connected to discharge the control terminals of the electronic switch when activated, and the aforementioned resistor connected to the electronic switch control terminals for preventing charge buildup on said control terminals when neither optical signal is present.

In the case of single-capacitor multiphasic shock systems, the electronic switch includes two high side electronic switches and two low side electronic switches connected in an H-bridge configuration for connecting the capacitor with selective polarity to a load. The H-bridge switch is connected at its low side to the low side of the single capacitor and a supply voltage at ground. Alternatively, the H-bridge switch may connect at its low side to the low side of the single capacitor and a supply voltage that is more negative than ground. The latter supply voltage is selected to be in the range from −5 to −20 V, more preferably, approximately −15 V.

In the application of the invention to an implantable cardiac defibrillator having an H-bridge switch for multiphasic shock delivery, one embodiment of the actuating means includes two isolated high side drivers for selectively operating each high side switch in response to a corresponding signal from the control circuits, and two low side drivers for selectively operating each low side switch in response to a corresponding signal from the control circuits, such that high side drivers are optically isolated in accordance with the present invention.

The control circuits for timing shocks operate first to actuate one of said high side drivers, and then after some preset time, to actuate the corresponding one of the two low side drivers, to begin each phase of a shock. Then, the control circuits first deactuate the one high side driver, and then, after some preset time, deactuate the corresponding low side driver, to end each phase of a shock. Alternatively, the control circuits may simultaneously deactuate the one high side driver and the corresponding one low side driver, to end each phase of a shock. The preset time between actuating the high and low side drivers, and deactuating the high and low side drivers when used, is preferably on the order of several hundred microseconds.

BRIEF DESCRIPTION OF THE DRAWINGS

Further features of the invention, its nature and various advantages will be apparent from the accompanying drawings and the following detailed description of the invention, in which like reference characters refer to like elements, and in which:

FIG. 2 is a schematic circuit diagram of the transmitter, receiver, and optical path for driving a single isolated switch of FIG. 1;

FIG. 3 is a schematic circuit diagram of a transmitter for a variant of the invention with one optical signal per driven isolated switch;

FIG. 4 is a schematic circuit diagram of a transmitter for another variant of the invention, with two optical signals per driven isolated switch;

DETAILED DESCRIPTION OF THE INVENTION

Figure 1:
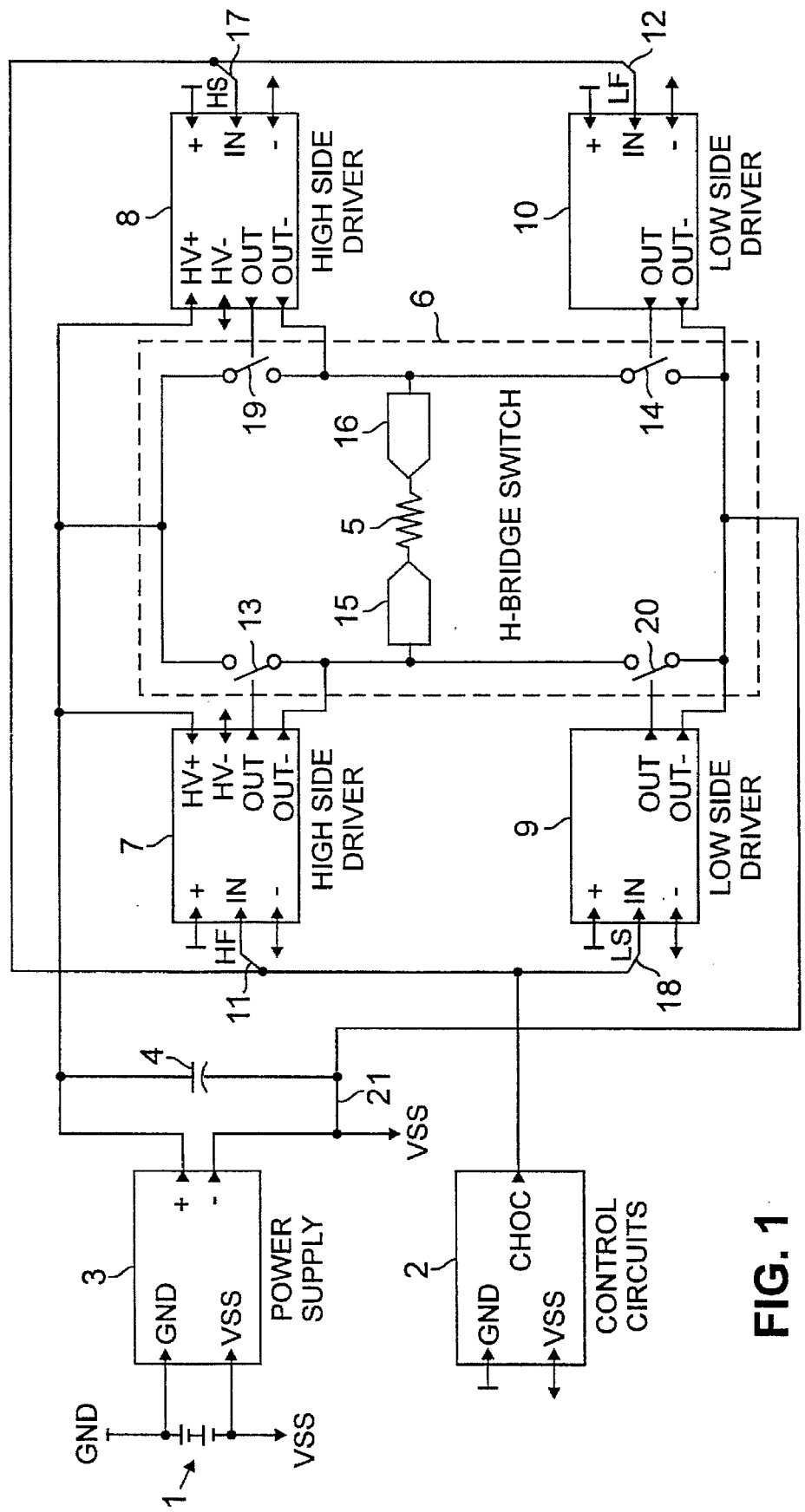
FIG. 1 is a block schematic diagram of a preferred embodiment of the present invention as applied to a multiphasic shock generator of an implantable defibrillator.

Referring to FIG. 1, a battery 1 supplies energy to the implantable defibrillator circuits, typically at 5 to 15 V. Control circuits 2, for timing shocks (i.e., when they occur, their duration, and the number, type and sequence of phases), provide control signals for electronic switches in the shock generator, in this example for providing single-capacitor biphasic shocks. A shock charging circuit 3 converts battery energy to shock energy, typically at 0.75 KV, stored on a capacitor at 4, which is typically 125 µF. These circuits are well known the art and any such circuit may be used. One useful circuit is described in copending and commonly assigned U.S. patent application Ser. No. 08/287, 834, filed Aug. 9, 1994 in the name of Peter Jacobson, the disclosure of which is incorporated herein by reference.

FIG. 1 shows an H-bridge configuration shock delivery circuit including an H-bridge switch 6, which acts as an electronic switch to connect capacitor 4 to a load 5 with a selected polarity. Also shown are high side drivers 7 and 8, and low side drivers 9 and 10, for actuating the individual electronic switches 13, 14, 19 and 20 in the H-bridge switch 6.

Figure 13:
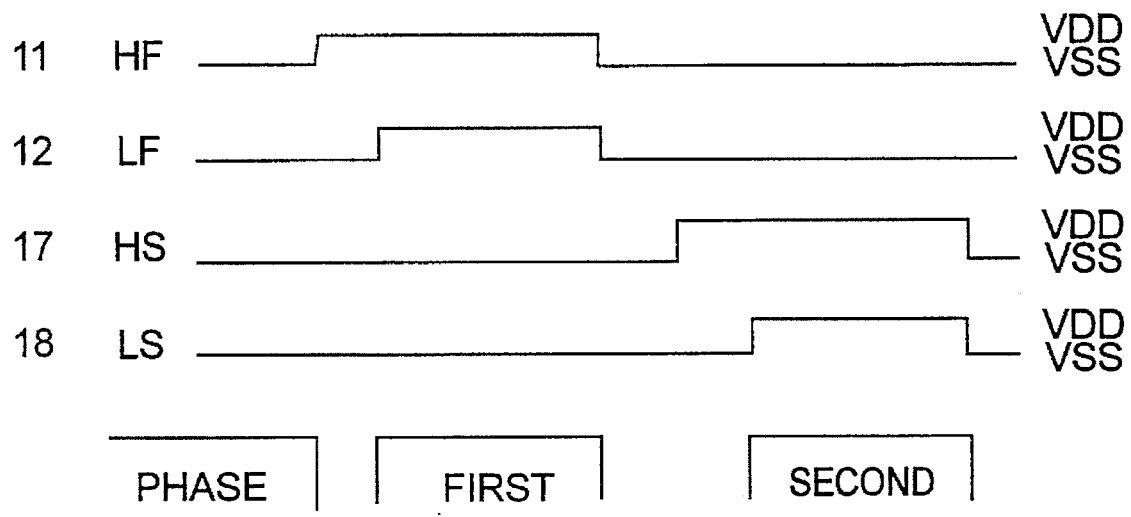
FIGS. 13 and 14 illustrate the timing of control signals for applying the method of the invention to a multiphasic shock generator.
Figure 14:
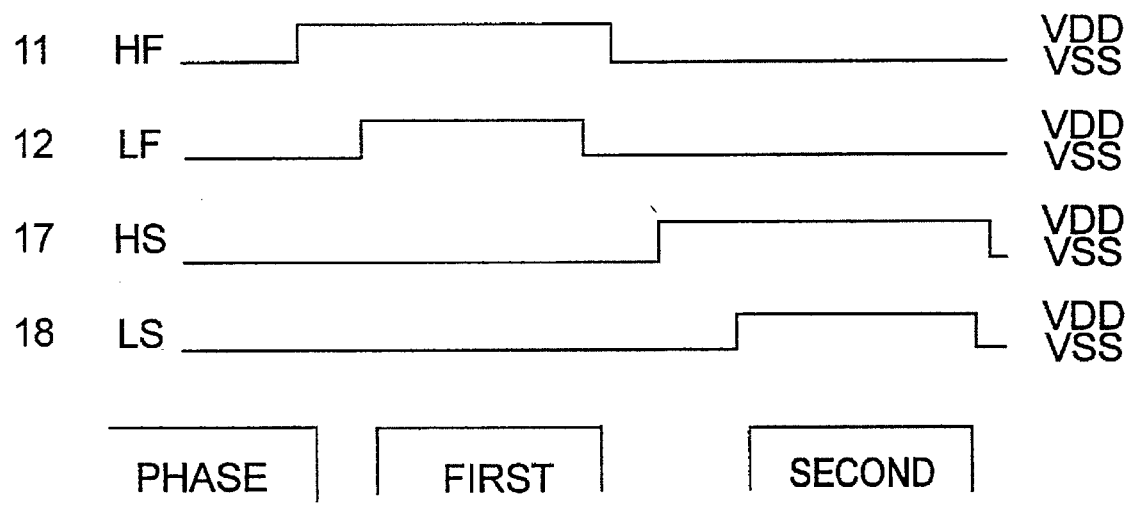

Referring to FIGS. 1, 13 and 14, when control circuits 2 assert HF at 11 and LF at 12, high side driver 7 and low side driver 10 convey these control signals to close switches 13 and 14 respectively. As a result, current flows from capacitor 4 through load 5 in a first direction, from shock electrode 15 to shock electrode 16 (this is the first shock phase). Then, control circuits 2 deassert the asserted outputs, more preferably all of the control outputs 11, 12, 17, 18, thereby opening all switches. This provides a delay between phases, giving time for all switches to open. Next, control circuits 2 assert HS at 17 and LS at 18, so that high side driver 8 and low side driver 9 close switches 19 and 20 respectively. Consequently, current flows from the capacitor 4 through load 5 in a second direction, from shock electrode 16 to shock electrode 15 (this is the second shock phase). Control circuits 2 next deassert the asserted outputs, more preferably all of the control outputs 11, 12, 17, 18, thereby opening all switches 13, 14, 19 and 20 and truncating the second phase. The control circuits 2 can optionally continue this sequence to generate additional phases.

Switches 13, 14, 19, and 20 illustrated in FIG. 1 can be implemented as MOSFETs or IGBTs, as is known to those of ordinary skill in the art. MOSFETs or IGBTs should have series diodes, as shown in prior art, to prevent external defibrillation from being conducted in the opposite direction through the switches. Switches should be rated at approximately 30 A and 1.0 KV, and should have off-state leakage not exceeding a few microamperes.

Low side drivers 9 and 10 shown in FIG. 1 can be implemented in a conventional manner, since they are not isolated. In general MOSFETs with an on-resistance of a few hundred ohms are used in a push-pull configuration. This gives a rise time and falltime of the control voltage on typical switch transistors 14, 20 of approximately 10 µs. A capacitor of a few nanofarads (not shown) may optionally be added across the output of the switch driver to control risetime and reduce the importance of the Miller effect. It is important to maintain a moderate slew rate for the shock pulse (on the order of a few amperes per microsecond) to reduce inductive and capacitive coupling of the shock pulse into other sensitive circuits in the implantable defibrillator, such as telemetry circuits and P-wave or R-wave sensing amplifiers.

The circuit illustrated in FIG. 1 further shows a connection 21 from the low side of capacitor 4 and the low side of the H-bridge switch 6, to a negative supply that is near ground. This permits operating control circuits 2 and low side drivers 9 and 10 between ground and this negative supply voltage, simplifying their circuitry, as described in a copending and commonly assigned application entitled Shock Generator For Implantable Defribillator/Cardiac Stimulator, filed Oct. 11, 1994 in the names of Alan H. Ostroff, Peter M. Jacobson, and Daniel P. Kroiss Ser. No. 08/220,854 (attorney docket 22094.9926), the disclosure of which is incorporated herein by reference. However, the invention could equally well be applied to shock generators which refer the low side to ground, and which isolate the low side.

Drivers 7, 8, 9, and 10 each comprise an input "in", an output "out" and a negative output "out–". References to "HV+" and "HV–" are to the high positive and high negative voltages, respectively.

Numerous variants of the circuit shown in FIG. 1 exist within the scope of the invention. For example, additional power supply circuitry could be used to provide separate negative voltage supplies for operating control circuits 2, pacing and sensing circuitry not shown, and the low side drivers 9 and 10, instead of operating these circuits directly from the battery. Also, level shifter circuits or voltage multipliers could be used to translate logic signals from one supply to the other. This additional circuitry is not shown here to preserve clarity.

FIG. 2 shows the transmitter 22, receiver 23, and optical path 24 for driving a single isolated switch. The transmitter 22 has power supply inputs "+" at 25 and "−" at 26, and a control signal input "in" at 27. Input 27 is a logic level signal operating between ground GND at 25 and supply VSS at 26. The receiver 23 has power supply inputs "HV+" at 28 and "HV−" at 29. It has an output signal "out" at 30, referred to "out−" at 31.

One embodiment of the invention uses only one optical path 24A per driven switch, and a second embodiment uses two optical paths 24A and 24B per driven switch.

When control circuits 2 shown in FIG. 1 apply a logic high state signal at "in" 27, then the transmitter sends an optical signal via path 24A to the optical receiver 23, which responds by asserting the "out" high at 30. When the control circuit 2 deasserts the "in" input to an output state, then, in the first variant of the invention the transmitter 22 stops sending the optical signal, and the receiver 23 responds by deasserting "out" at 30 to a low state. In the second variant the transmitter 22 stops sending the first optical signal when it is time to open the switch in the H-bridge switch and sends at least a brief pulse of a second optical signal, via path 24B, to which the receiver 23 responds and shuts off the output at 30.

Referring to FIG. 3, a transmitter circuit for the first variant of invention described above is shown, using a single optical path 24A. When the control circuits 2 (FIG. 1) assert "in" at 27 to a high level, this turns on the N-channel MOSFET at 34, allowing current to flow through limiting resistor 32 and light-emitting-diode (LED) 33, until control circuits 2 return the "in" input to a low level. Typical LED current is approximately 30 to 100 mA. While current flows, the LED 33 sends light along the optical path 24A (FIG. 2) to convey control signal information to the optical receiver 23 (FIG. 2). The presence of this optical signal signals the receiver 23 to turn on the electronic switch, and its absence signals the receiver 23 to turn off the electronic switch.

Referring now to FIG. 4, a transmitter circuit for the second variant of the invention described above is shown, using two optical paths 24A and 24B. Components 25 to 27 and 32 to 34 operate as described in the explanation of FIG. 3, except that there are two optical paths 24A, 24B. LED 33 emits over path 24A only. Thus the transmitter 22 emits a first optical signal whose presence signals the receiver 23 to turn on the controlled electronic switch. When the control circuits 2 deassert "in" at 27 to a low level, this extinguishes the LED at 33 and triggers monostable multivibrator 35. The monostable times a period of approximately 0.10 ms where its Q output at 36 remains high. The Q output at 36 being high turns on N-channel MOSFET 39, allowing current to flow through limiting resistor 37 and LED 38, again, typically approximately 30 to 100 mA. LED 38 sends light along a second optical path 24B shown in FIG. 2. The presence of this second optical signal instructs the receiver 23 in FIG. 2 to shut off the controlled switch.

Figure 5:
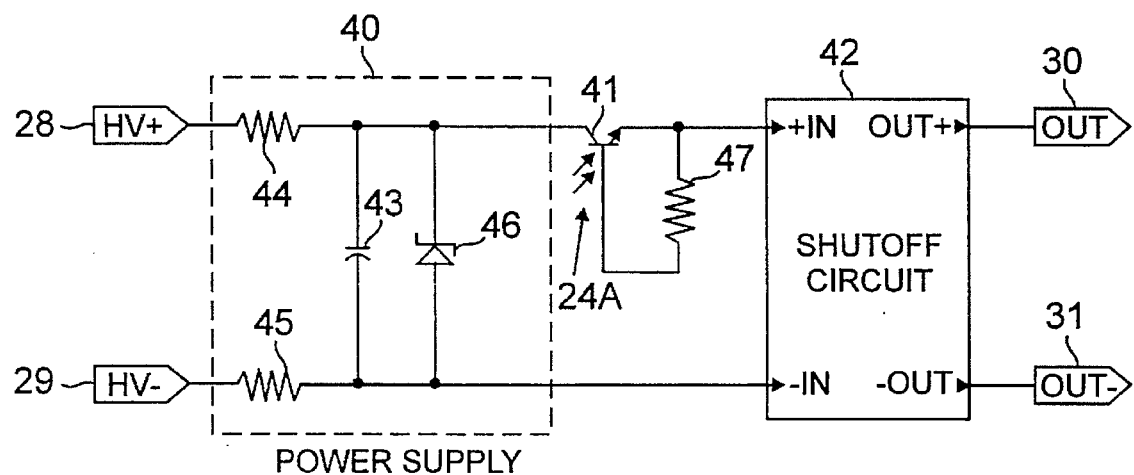
FIG. 5 is a schematic circuit diagram of a receiver for a variant of the invention using an isolated power supply and a phototransistor.

Referring to FIG. 5, a receiver circuit 23 is shown. It includes power supply 40 to provide power for charging the control terminals of the controlled electronic switch, and a phototransistor switch 41 for conducting current from power supply 40 to the control terminals of the controlled switch, when activated by an optical signal along optical path 24A (FIG. 2). Resistor 47, typically 0.47 MOhms, helps shut off phototransistor 41 more rapidly. Also shown in FIG. 5 is a shutoff circuit 42 for discharging the control terminals of the controlled switch when either the phototransistor switch 41 ceases to supply a charging current, as in the first variant of the invention, or when the shutoff circuit 42 receives a second optical signal along path 24B (not shown in FIG. 5), as in the second variant of the invention.

The power supply 40 illustrated in FIG. 5 includes a capacitor 43, typically 50 nF, for storing energy at low voltage, and a current limited path with high value resistors 44 and 45, to connect capacitor 43 to charge across the high voltage supply capacitor 4 of the defibrillator generator circuit shown in FIG. 1. Since the resistor value is high, typically 10 MOhms, only low current flows in the load 5 in FIG. 1 due to resistors 44 and 45. (It is evident that when power supply 40 is used in conjunction with the discharge circuits shown in FIG. 8, 10, or 12, this current can be reduced to a very low value due to blocking diodes 57, 58 shown in those circuits.) The power supply 40 also has a voltage limiter at 46 to prevent overcharging of capacitor 43. Limiter 46 can be, for example, a zener diode with a zener voltage of approximately 15 V.

Figure 6:
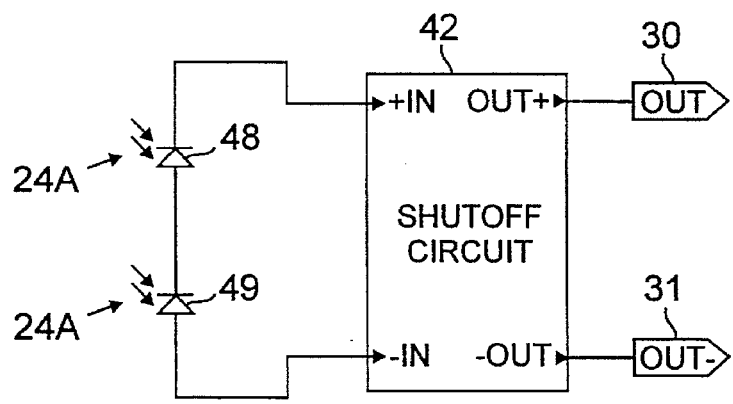
FIG. 6 is a schematic circuit diagram of a receiver for another variant of the invention, using photodiodes.

Referring to FIG. 6, an alternate optical receiver 23 is shown which uses at least one photodiode (two are shown at 48 and 49) to replace the power supply 40 and the phototransistor switch 41 of the circuit shown in FIG. 5. In this embodiment, the photodiodes 48, 49 provide the charging current to the control terminals of the controlled electronic switch in response to the optical signal at path 24A. The photodiodes 48, 49 provide a current which is a few percent of the current in the transmitter 23 LED 33, at a few volts per photodiode, without any other power supply. Advantageously, this considerably simplifies circuitry and reduces component count. Further, it is possible to place additional photodiodes in series to increase the output voltage, or in parallel to increase the current for controlling the selected electronic switch. In general it is advisable to provide at least 0.15 mA at 15 V to control typical MOSFET or IGBT switches.

Also shown in FIG. 6 is a shutoff circuit 42 to discharge the control terminals of the controlled switch, as explained in the circuit shown in FIG. 5.

Figure 7:
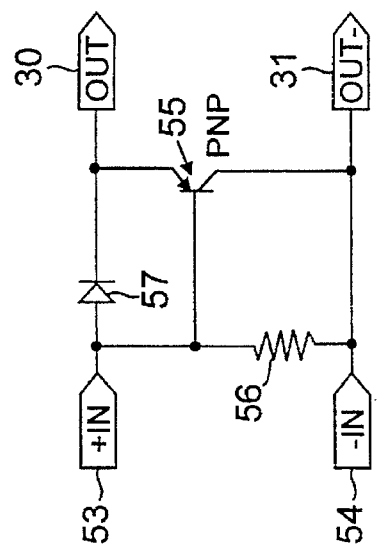
FIG. 7 is a schematic circuit diagram of a shutoff circuit for use with the variant of the invention having two optical paths per driven isolated switch.

Referring to FIGS. 7 through 12, different constructions of shutoff circuits 42 are shown. The circuit illustrated in FIG. 7 is for use with the second variant of the invention described above with two optical paths, and the circuits of FIGS. 8–12 are for use with the first variant having a single optical path. Each of these circuits connects with inputs 53 and 54 to the current generators shown in FIGS. 5 and 6. Current enters terminal 53 and leaves via 54. Each of these circuits also connects with outputs 30 and 31 across the control terminals of the controlled electronic switch. When the shutoff circuit 42 is activated, it discharges the control terminals by providing a low resistance path from 30 to 31.

Referring now to the circuit in FIG. 7, it is activated by an optical signal on path 24A as described above. This turns on phototransistor 50, providing a low resistance path from 30 to 31. Resistor 51, typically 0.47 MOhms, increases the noise immunity of the phototransistor 50. Resistor 52, typically 1.0 MOhms, prevents charge buildup on the control terminals 30 and 31 which could falsely trigger a shock, during the period between shocks.

Illustrated in FIGS. 8 through 12 are shutoff circuits 42 which are normally activated, and are deactivated by current entering terminal 53 and leaving terminal 54. In this manner these circuits normally hold the controlled electronic switch (whose control terminals are across 30 and 31) off, until the power supply and phototransistor or photocoupler circuitry shown in FIGS. 5 and 6 supply current to turn on the controlled electronic switch. Each circuit uses a transistor 55 to provide a low impedance path from terminals 30 to 31. Each circuit has a biasing resistor 56, typically 1.5 MOhms, to hold the transistor 55 on when no current flows between input terminals 53 and 54. Each circuit uses one or two small signal diodes, typically rated at 0.10 A and 15 PIV, at 57 and 58, which provide a voltage drop to bias the transistor off, when current flows to switch control terminals 30, 31.

Figure 8:
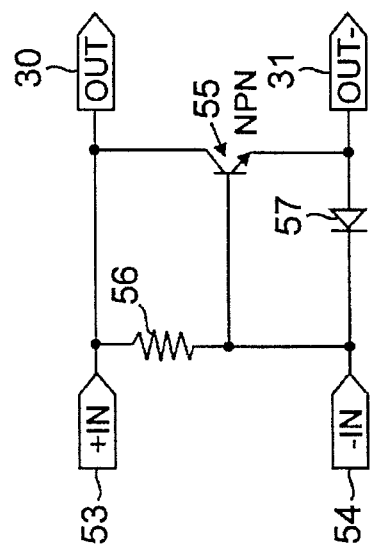

The shutoff circuit shown in FIG. 8 is implemented with a depletion-type N-channel MOSFET, which is on with a gate-source voltage of zero, and off when the gate voltage is a few volts more negative than the source.

Figure 9:
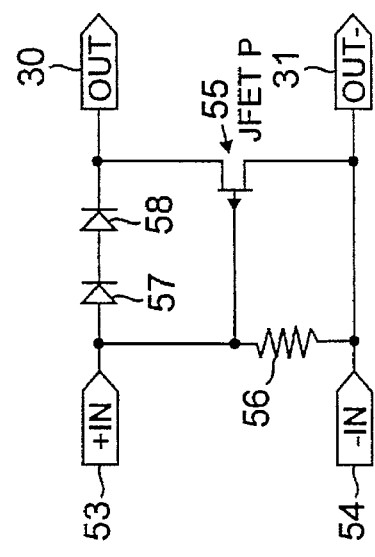
FIGS. 8 through 12 are schematic circuit diagrams of alternate shutoff circuits for use with the variant of the invention having one optical path per driven isolated switch.

The circuit shown in FIG. 9 uses a P-channel junction field-effect transistor (JFET) which is on with a gate-source voltage of zero, and off when the gate voltage is a few volts more positive than the source.

Figure 10:
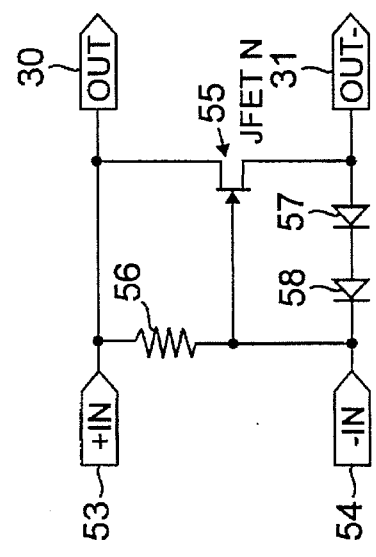

The circuit shown in FIG. 10 uses an N-channel JFET, which operates like the depletion-type N-channel MOSFET shown in FIG. 8.

Figure 11:
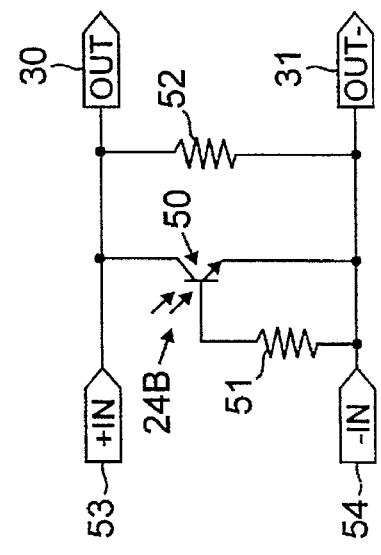

The circuit shown in FIG. 11 uses a bipolar PNP transistor, which is on when the emitter is about 0.7 V more positive than the base. Thus as soon as switch control terminal 30 rises above this value with respect to terminal 31, and no current flows through diode 57, then transistor 53 is on and holds the control voltage to about 0.7 V maximum. When current flows through diode 57 to turn on the controlled switch, this turns off transistor 53.

Figure 12:
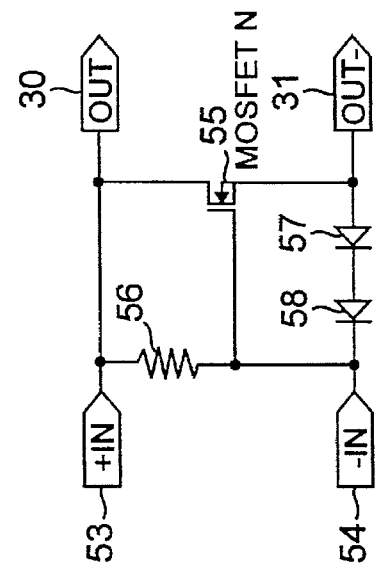

The circuit shown in FIG. 12 uses a bipolar NPN transistor, which is on when the base is about 0.7 V more positive than the emitter. The circuit operates similarly to the circuit shown in FIG. 11.

FIGS. 13 and 14 show the timing of the four switch control signals shown in FIG. 1. Each signal actuates a switch driver, which in turn actuates a switch, as shown in the table below:

| signal name | signal number | driver number | switch number |
| --- | --- | --- | --- |
| HF | 11 | 7 | 13 |
| LF | 12 | 10 | 14 |
| HS | 17 | 8 | 19 |
| LS | 18 | 9 | 20 |

Isolated high side drivers using optical coupling, and especially those using photodiodes, can take a relatively long time to turn on or off the controlled transistor. This can be on the order of several hundred microseconds, depending on the efficiency of the optical transfer and the current in the transmitter LED.

When a switch turns on or off while passing current, this is called hot switching. The switch must dissipate power during hot switching. The energy the switch must dissipate is the product of the current through the switch and the voltage across the switch, integrated over the transition time. If hot switching is used, it is necessary to limit the transition time to a few tens of microseconds with practical switches for implantable shock generators. On the other hand, the transition time should not be too short, since high rates of change of current or voltage can couple inductively or capacitively to sensitive points elsewhere in the circuit.

Since there are two switches in series for each phase of the shock in the H-bridge configuration shown in FIG. 1, only one switch needs to undergo hot switching. Accordingly, the present invention performs hot switching on the low side, or where no isolation is used and it is simple to control turn-on and turn-off time.

For this reason, to provide a shock phase, control circuits 2 first assert HF at 11, and then wait a preset time period of, for example, several hundred microseconds, to allow time for high side driver 7 to turn on switch 13, before asserting LF at 12. In this manner, switch 13 is already on when switch 14 starts to turn on. There is no hot switching at switch 13. Thus the rate of turning on switch 14 determines the slew rate of the defibrillation shock. Low side driver 10 is constructed as described in the explanation of FIG. 1 above to provide controlled shock slew rate.

At the end of the first phase, the control circuits 2 can first instruct the low side driver 10 to turn off switch 14, as shown in FIG. 14. Or, if the turn-off time of switch 13 produced by the shutoff circuit 42 in high side driver 7 is adequate, the control circuits can simultaneously instruct the low side driver and high side driver to turn off their switches, as shown in FIG. 13. The control circuits 2 similarly produce the second phase.

One foreseeable modification to the foregoing embodiments within the scope of the invention is to configure a floating output stage, as in early implantable defibrillators. In this case the optical drivers of the invention can be used to drive low side switches as well as high side switches, provided a rapid driver is used for at least one series switch in each shock phase, to limit transition times as explained above. A single transmitter could drive multiple receivers to operate simultaneously multiple switches for each phase in a multiphasic discharger.

Another foreseeable modification within the scope of the invention is to implement the discharger with high voltage P-channel MOSFETs, P-type IGBTs, or PNP bipolar transistors, inverting the version shown above, should high-voltage versions of such devices become available in the future.

Although the invention has been described with reference to particular embodiments, it is to be understood that these embodiments are merely for purposes of illustration, and not of limitation, of the application of the principles of the invention. Numerous other modifications may be made and other arrangements may be devised without departing from the spirit and scope of the present invention.

We claim:

1. A shock delivery circuit, comprising:

a battery having stored energy;

a control circuit having an electrical output signal to time a shock;

a shock charging circuit coupled to the battery and operable to convert battery energy to shock energy, the shock charging current having an output;

a first capacitor coupled to the shock charging circuit output to store shock energy;

a controllable electronic switch having an open state and a closed state, selectively connecting said first capacitor to a load;

an optical transmitter receiving said electrical output signal from said control circuit and emitting an optical signal corresponding to said electrical output signal;

an optical receiver receiving said optical signal and generating therefrom an electrical control signal corresponding to said optical signal to control said electronic switch state; and an electrically isolated optical path conveying said optical signal from said optical transmitter to said optical receiver.

2. The apparatus of claim 1 wherein said emitted optical signal has a first level that signals said optical receiver to close said electronic switch, and a second level that signals said optical receiver to open said electronic switch.

3. The apparatus of claim 2 wherein said electronic switch further comprises a control terminal receiving said electrical control signal to open and close said electronic switch in response to said electrical control signal, and wherein said optical receiver comprises:

at least one photodiode to provide selectively a charging current to said control terminal to close said electronic switch in response to the optical signal having said first level, and a shutoff circuit coupled to discharge said control terminal to open said electronic switch in response to the absence of said charging current.

4. The apparatus of claim 3 wherein said shutoff circuit comprises a transistor connected to said control terminal to discharge said control terminal and open said electronic switch when said photodiode no longer supplies said charging current.

5. The apparatus of claim 1 wherein said optical transmitter optical signal further comprises a first optical signal and a second optical signal, the electrically isolated optical path further comprises first and second electrically isolated optical paths respectively conveying said first and second optical signals to said optical receiver, the first optical signal indicating to said optical receiver to turn on said electronic switch, and the second optical signal indicating to said optical receiver to turn off said electronic switch.

6. The apparatus of claim 5 wherein said electronic switch further comprises a control terminal receiving a signal to open and close electronic switch, and wherein said optical receiver comprises:

a power supply;

a first phototransistor switch to conduct selectively a charging current from said power supply to said control terminal to close said electronic switch in response to said first optical signal; and a shutoff circuit coupled to discharge said control terminal to open said electronic switch in response to the second optical signal.

7. The apparatus of claim 6 where said power supply comprises:

a second capacitor for storing energy at low voltage;

a current-limited path, comprising at least one high-value resistor, to charge said second capacitor from said first capacitor; and a voltage limiter to prevent said second capacitor from charging to a voltage beyond a preset voltage.

8. The apparatus of claim 7 wherein said voltage limiter comprises a zener diode.

9. The apparatus of claim 6 wherein said shutoff circuit further comprises:

a second phototransistor switch connected to discharge said control terminal to open said electronic switch in response to the second optical signal.

10. The apparatus of claim 9 wherein the shutoff circuit further comprises a resistor connected to said control terminal to minimize charge buildup in the absence of the first and second optical signals.

11. The apparatus of claim 5 where said electronic switch further comprises a control terminal receiving a signal to open and close said electronic switch, and wherein said optical receiver comprises:

at least one photodiode to provide selectively a charging current to said control terminal to close said electronic switch in response to the first optical signal; and a shutoff circuit coupled to discharge said control terminal to open said electronic switch in response to the said second optical signal.

12. The apparatus of claim 11 where said shutoff circuit comprises a phototransistor connected to discharge said control terminal to open said electronic switch in response to the second optical signal.

13. The apparatus of claim 12 wherein the shutoff circuit further comprises a resistor connected to minimizes charge buildup on said control terminals in the absence of the first and second optical signals.

14. The apparatus of claim 1 further comprising a ground and a supply voltage at ground, where the first capacitor has a high side and a low side and said electronic switch further comprises an H-bridge switch having two high side switches respectively connected to two shock electrodes and to two low side switches, the high side switches being coupled to said first capacitor high side and the low side switches being coupled to said first capacitor low side and said supply voltage, and further comprising means for selectively operating one of said two high side switches and one of said two low side switches in response to said control circuit electrical output signal to connect said first capacitor with a selected polarity to said load across said shock electrodes, wherein the high side switches are electrically isolated from said control circuit electrical output signal.

15. The apparatus of claim 1 further comprising a ground and a supply voltage at ground, where the first capacitor has a high side and a low side and said electronic switch further comprises an H-bridge switch having two high side switches respectively connected to two shock electrodes and to two low side switches, the high side switches being coupled to said first capacitor high side and the low side switches being coupled to said first capacitor low side and said supply voltage, means for selectively operating one of said two high side switches and one of said two low side switches in response to said control circuit electrical output signal to connect said first capacitor with a selected polarity to said load across said shock electrodes, wherein the high side switches are electrically isolated from said control circuit electrical output signal, wherein said control circuit electrical output signal further comprises a first signal corresponding to operating selectively one of said two high side switches and a second signal corresponding to operating one of said two low side switches, and two isolated high side drivers respectively connected to operate the two high side switches, each isolated high side driver having an input for a said first signal and electrically isolating said high side switch from said first signal; and two low side drivers connected to operate selectively the two low side switches in response to a said second signal from said control circuit.

16. The apparatus of claim 15 where said control circuit first signal actuates one of the two isolated high side drivers to turn on the corresponding one high side switch, and then after a first preset time said control circuit second signal actuates the corresponding one of the two low side drivers to turn on the corresponding one low side switch, thereby to begin a phase of said shock.

17. The apparatus of claim 16 where said control circuit first and second signals further operate to deactuate the one high side driver, and then after a second preset time deactuate the corresponding one low side driver, thereby to end said phase of shock.

18. The apparatus of claim 16 where said control circuits first and second signals further operate to deactuate simultaneously said one high side driver and said corresponding one low side driver, thereby to end said phase of shock.

19. The apparatus of claim 16 where said first preset time is on the order of several hundred microseconds.

20. The apparatus of claim 1 further comprising a ground and a supply voltage that is more negative than ground, wherein the first capacitor has a high side and a low side and said electronic switch further comprises an H-bridge switch having two high side switches respectively connected to two shock electrodes and to two low side switches, the high side switches being coupled to said first capacitor high side and the low side switches being coupled to said first capacitor low side and said supply voltage, and means for selectively operating one each of said two high side switches and said two low side switches in response to said control circuit electrical output signal to connect said first capacitor with a selected polarity to said load across said shock electrodes, wherein the high side switches are electrically isolated from said control circuit electrical output signal.

21. The apparatus of claim 20 wherein said supply voltage is in the range from −5 to −20 V.

22. The apparatus of claim 1 further comprising a ground and a supply voltage that is more negative than ground, wherein the first capacitor has a high side and a low side and said electronic switch further comprises an H-bridge switch having two high side switches respectively connected to two shock electrodes and to two low side switches, the high side switches being coupled to said first capacitor high side and the low side switches being coupled to said first capacitor low side and said supply voltage, wherein said control circuit electrical output signal further comprises a first signal corresponding to operating selectively one of said two high side switches and a second signal corresponding to operating one of said two low side;

two isolated high side drivers respectively connected to operate selectively the two high side switches, each isolated high side driver having an input for a said first signal and electrically isolating said high side switch from said first signal; and two low side drivers connected to operate selectively the two low side electronic switch in response a said second signal from said control circuit.

23. The apparatus of claim 22 wherein said control circuit further comprises a first timer to time a first preset time and wherein said control circuit first and second signals further operate to actuate one of the two isolated high side drivers to turn on the corresponding one high side switch, and then after the first preset time actuate the corresponding one of said two low side drivers to turn on the corresponding one low side switch, thereby to begin a phase of said shock.

24. The apparatus of claim 23 wherein said control circuit further comprises a second timer to time a second preset time and wherein said control circuit first and second signals further operate to deactuate the one high side driver, and then after the second preset time deactuate the corresponding one low side driver, thereby to end said phase of shock.

25. The apparatus of claim 23 where said control circuit first and second signals further operate to deactuate simultaneously said one high side driver and the corresponding one low side driver, thereby to end said phase of shock.

26. The apparatus of claim 23 where said first preset time is on the order of several hundred microseconds.

27. A method of delivering cardiac defibrillating shock phases comprising:

a) charging a capacitor to store shock energy;

b) generating a first electrical control signal corresponding to a timed discharge of the capacitor to deliver a shock phase;

c) converting the first electrical control signal into a first optical signal corresponding to the start of the shock phase and a second optical signal corresponding to the end of the shock phase;

d) passing the first and second optical signals over separate respective first and second electrically isolated optical paths;

e) converting the first and second optical signals into first and second switch control signals respectively;

f) applying the first and second switch control signals to a control terminal of an electronic switch having an open state, a closed state, said control terminal controlling the electronic switch state in response to said first and second switch control signals, and applying a first signal to the control terminal to close the electronic switch in response to the first switch control signal, and applying a second signal to discharge the control terminal and open the electronic switch in response to the second switch control signal; and g) placing the electronic switch in the closed condition for said timed discharge according to said second electrical control signal to deliver said shock phase.

28. The method of claim 27 further comprising controlling the shock phase time by changing the first electrical control signal magnitude for a duration corresponding to said shock phase time.

29. The method of claim 27 further comprising biasing said electronic switch in the open condition by discharging the control terminal in the absence of said optical signal.

30. The method of claim 27 further comprising minimizing the accumulation of any charge on the control terminal in the absence of said optical signal.

31. The method of claim 27 wherein step f) comprises in part:

providing an H-bridge switch having two shock electrodes interposed between two high side switches and two low side switches, each switch having an open state, a closed state, and a control terminal to open and close the switch in response to a control signal; and connecting the two high side switches to a high side of the capacitor and connecting the low side switches to the low side of the capacitor; and wherein steps b)–f) further comprise i) generating a first control signal for operating one of said high side switches and a second control signal for operating one of the low side switches, ii) converting said first control signal to an optical signal, passing said optical signal over one of said first and second electrically isolated optical paths and converting said optical signal to said one corresponding switch control signal, applying said one corresponding switch control signal to said one high side switch and closing said switch, and iii) closing the corresponding one low side switch in response to one corresponding switch control signal.

32. The method of claim 31, wherein steps i) and ii) further comprise generating a first optical signal corresponding to the start of the shock phase and a second optical signal corresponding to the end of the shock phase, and placing said one high side switch in the closed condition in response to said first optical signal and placing said one high side switch in the open condition in response to said the second optical signal.

33. The method of claim 31 further comprising terminating the first and second control signals simultaneously and placing said corresponding one high and low side switches in the open condition to end the shock phase.

34. The method of claim 31 further comprising providing a voltage supply and a ground and connecting the low side of the H-bridge switch and capacitor to said voltage supply.

35. The method of claim 34 wherein providing a voltage supply further comprises providing a voltage supply that is more negative than said ground.

36. The method of claim 31 wherein step i) further comprises generating the first control signal for a first time having a start and an end, generating the second control signal for a second time having a start and an end, and starting the second time after the start of the first time.

37. The method of claim 36 further comprising ending the second time prior to the end of the first time.

38. The method of claim 36 wherein starting the second time after the first time further comprises starting the second time several hundred microseconds after the first time.

39. A shock delivery circuit, comprising:

a battery having stored energy;

a control circuit having an electrical output signal to time a shock;

a shock charging circuit coupled to the battery and operable to convert battery energy to shock energy, the shock charging current having an output;

a first capacitor coupled to the shock charging circuit output to store shock energy;

a controllable electronic switch having an open state and a closed state, selectively connecting said first capacitor to a load;

an optical isolation circuit optically coupling the control circuit electrical output signal to the electronic switch to control said electronic switch to deliver shock energy to the load when the electronic switch is closed;

a ground and a supply voltage at ground, where the first capacitor has a high side and a low side and said electronic switch further comprises an H-bridge switch having two high side switches respectively connected to two shock electrodes and to two low side switches, the high side switches being coupled to said first capacitor high side and the low side switches being coupled to said first capacitor low side and said supply voltage, and wherein the optical isolation circuit further comprises means for selectively operating one of said two high side switches and one of said two low side switches in response to said control circuit electrical output signal to connect said first capacitor with a selected polarity to said load across said shock electrodes, wherein the high side switches are electrically isolated from said control circuit electrical output signal, wherein said control circuit electrical output signal further comprises a first signal corresponding to operating selectively one of said two high side switches and a second signal corresponding to operating one of said two low side switches, and wherein said optical isolation circuit further comprises:

two isolated high side drivers respectively connected to operate the two high side switches, each isolated high side driver having an input for a said first signal and electrically isolating said high side switch from said first signal; and two low side drivers connected to operate selectively the two low side switches in response to a said second signal from said control circuit.

40. The apparatus of claim 39 where said control circuit first signal actuates one of the two isolated high side drivers to turn on the corresponding one high side switch, and then after a first preset time said control circuit second signal actuates the corresponding one of the two low side drivers to turn on the corresponding one low side switch, thereby to begin a phase of said shock.

41. The apparatus of claim 40 where said control circuit first and second signals further operate to deactuate the one high side driver, and then after a second preset time deactuate the corresponding one low side driver, thereby to end said phase of shock.

42. The apparatus of claim 40 where said control circuits first and second signals further operate to deactuate simultaneously said one high side driver and said corresponding one low side driver, thereby to end said phase of shock.

43. The apparatus of claim 40 where said first preset time is on the order of several hundred microseconds.

44. A shock delivery circuit, comprising:

a battery having stored energy;

a control circuit having an electrical output signal to time a shock;

a shock charging circuit coupled to the battery and operable to convert battery energy to shock energy, the shock charging current having an output;

a first capacitor coupled to the shock charging circuit output to store shock energy;

a controllable electronic switch having an open state and a closed state, selectively connecting said first capacitor to a load;

an optical isolation circuit optically coupling the control circuit electrical output signal to the electronic switch to control said electronic switch to deliver shock energy to the load when the electronic switch is closed;

a ground and a supply voltage that is more negative than ground, wherein the first capacitor has a high side and a low side and said electronic switch further comprises an H-bridge switch having two high side switches respectively connected to two shock electrodes and to two low side switches, the high side switches being coupled to said first capacitor high side and the low side switches being coupled to said first capacitor low side and said supply voltage, and wherein the optical isolation circuit further comprises means for selectively operating one each of said two high side switches and said two low side switches in response to said control circuit electrical output signal to connect said first capacitor with a selected polarity to said load across said shock electrodes, wherein the high side switches are electrically isolated from said control circuit electrical output signal.

45. The apparatus of claim 44 wherein said supply voltage is in the range from −5 to −20 V.

46. A shock delivery circuit, comprising:

a battery having stored energy;

a control circuit having an electrical output signal to time a shock;

a shock charging circuit coupled to the battery and operable to convert battery energy to shock energy, the shock charging current having an output;

a first capacitor coupled to the shock charging circuit output to store shock energy;

a controllable electronic switch having an open state and a closed state, selectively connecting said first capacitor to a load;

an optical isolation circuit optically coupling the control circuit electrical output signal to the electronic switch to control said electronic switch to deliver shock energy to the load when the electronic switch is closed;

a ground and a supply voltage that is more negative than ground, wherein the first capacitor has a high side and a low side and said electronic switch further comprises an H-bridge switch having two high side switches respectively connected to two shock electrodes and to two low side switches, the high side switches being coupled to said first capacitor high side and the low side switches being coupled to said first capacitor low side and said supply voltage, wherein said control circuit electrical output signal further comprises a first signal corresponding to operating selectively one of said two high side switches and a second signal corresponding to operating one of said two low side and wherein said optical isolation circuit further comprises:

two isolated high side drivers respectively connected to operate selectively the two high side switches, each isolated high side driver having an input for a said first signal and electrically isolating said high side switch from said first signal; and two low side drivers connected to operate selectively the two low side electronic switch in response a said second signal from said control circuit.

47. The apparatus of claim 46 wherein said control circuit further comprises a first timer to time a first preset time and wherein said control circuit first and second signals further operate to actuate one of the two isolated high side drivers to turn on the corresponding one high side switch, and then after the first preset time actuate the corresponding one of said two low side drivers to turn on the corresponding one low side switch, thereby to begin a phase of said shock.

48. The apparatus of claim 47 wherein said control circuit further comprises a second timer to time a second preset time and wherein said control circuit first and second signals further operate to deactuate the one high side driver, and then after the second preset time deactuate the corresponding one low side driver, thereby to end said phase of shock.

49. The apparatus of claim 47 where said control circuit first and second signals further operate to deactuate simultaneously said one high side driver and the corresponding one low side driver, thereby to end said phase of shock.

50. The apparatus of claim 47 where said first preset time is on the order of several hundred microseconds.

51. A method of delivering cardiac defibrillating shock phases comprising:

a) charging a capacitor to store shock energy;

b) generating first electrical control signal corresponding to a timed discharge of the capacitor to deliver a shock phase;

c) converting the first electrical control signal into an optical signal;

d) passing the optical signal over an electrically isolated optical path;

e) converting the passed optical signal to a second electrical control signal;

f) applying the second electrical control signal to a control terminal of an electronic switch having an open state, a closed state, said control terminal controlling the electronic switch state in response to said second electrical control signal; and g) placing the electronic switch in the closed condition for said timed discharge according to said second electrical control signal to deliver said shock phase;

wherein step f) comprises in part:

providing an H-bridge switch having two shock electrodes interposed between two high side switches and two low side switches, each switch having an open state, a closed state, and a control terminal to open and close the switch in response to a control signal; and connecting the two high side switches to a high side of the capacitor and connecting the low side switches to the low side of the capacitor; and wherein steps b)–f) further comprise i) generating a first control signal for operating one of said high side switches and a second control signal for operating one of the low side switches, ii) converting said first control signal to an optical signal, passing said optical signal over said electrically isolated optical path and converting said optical signal to said second electrical control signal, applying said second electrical control signal to said one high side switch and closing said switch, and iii) closing the corresponding one low side switch in response to the second control signal.

52. The method of claim 51, wherein steps i) and ii) further comprise generating a first optical signal corresponding to the start of the shock phase and a second optical signal corresponding to the end of the shock phase, and placing said one high side switch in the closed condition in response to said first optical signal and placing said one high side switch in the open condition in response to said the second optical signal.

53. The method of claim 51 further comprising terminating the first and second control signals simultaneously and placing said corresponding one high and low side switches in the open condition to end the shock phase.

54. The method of claim 51 further comprising providing a voltage supply and a ground and connecting the low side of the H-bridge switch and capacitor to said voltage supply.

55. The method of claim 54 wherein providing a voltage supply further comprises providing a voltage supply that is more negative than said ground.

56. The method of claim 51 wherein step i) further comprises generating the first control signal for a first time having a start and an end, generating the second control signal for a second time having a start and an end, and starting the second time after the start of the first time.

57. The method of claim 56 further comprising ending the second time prior to the end of the first time.

58. The method of claim 56 wherein starting the second time after the first time further comprises starting the second time several hundred microseconds after the first time.

* * * * *